(12) United States Patent
Chang

(10) Patent No.: US 8,083,196 B2
(45) Date of Patent: Dec. 27, 2011

(54) SUPPORT MECHANISM FOR OPERATION AUXILIARY TOOLS

(75) Inventor: Jen-Kun Chang, Yangmei Township, Taoyuan County (TW)

(73) Assignee: United Orthopedic Corporation, Hsinchu (TW)

( * ) Notice: Subject to any disclaimer, the term of this patent is extended or adjusted under 35 U.S.C. 154(b) by 0 days.

(21) Appl. No.: 12/196,364

(22) Filed: Aug. 22, 2008

(65) Prior Publication Data
US 2011/0253653 A1   Oct. 20, 2011

(51) Int. Cl.
*E04G 3/00* (2006.01)
(52) U.S. Cl. ............... 248/276.1; 248/278.1; 248/282.1
(58) Field of Classification Search ............... 248/276.1, 248/278.1, 282.1, 284.1, 176.1, 126
See application file for complete search history.

(56) References Cited

U.S. PATENT DOCUMENTS

| | | | |
|---|---|---|---|
| 6,209,835 B1 * | 4/2001 | Walrath et al. | 248/276.1 |
| 6,896,230 B2 * | 5/2005 | Cvek | 248/276.1 |
| 7,364,127 B2 * | 4/2008 | Huang | 248/276.1 |
| 7,464,909 B2 * | 12/2008 | Li | 248/280.11 |
| 7,922,137 B2 * | 4/2011 | Derry et al. | 248/274.1 |

* cited by examiner

*Primary Examiner* — Amy J Sterling
(74) *Attorney, Agent, or Firm* — Muncy, Geissler, Olds & Lowe, PLLC

(57) ABSTRACT

A support mechanism for operation auxiliary tools includes a fixing unit, a support lever movably mounted on the fixing unit, a first bar movably connecting with an end of the support lever, a limiting unit engaging with another end of the first bar, and a second bar connecting with the limiting unit. The fixing unit engages with the operation bed, and operation auxiliary tools are placed on the second bar. The support lever, the first bar and the second bar are adjusted freely and positioned by the limiting unit. The limiting unit maintains the first bar and the second bar at desired freedom. The support mechanism is placed firmly with a predetermined angle and position, making operations more stable.

7 Claims, 4 Drawing Sheets

SUPPORT MECHANISM FOR OPERATION AUXILIARY TOOLS

BACKGROUND OF THE INVENTION a) Field of the Invention

The present invention relates to a support mechanism for operation auxiliary tools, and particularly to a support mechanism for operation auxiliary tools which is adjustable in angle and height.

b) Description of the Prior Art

A conventional support mechanism for operation auxiliary tools 8, as shown in FIG. 4, generally comprises a fixing base 80 and an adjusting member 81 on a bottom of the fixing base 80. A tightwire 82 extends through the fixing base 80 and links with the adjusting member 81. A plurality of sleeves 83 extends through the tightwire 82 and couples with each other. A clamp 84 is provided on a top sleeve 83 and links with the tightwire 82. When a surgeon performs an operation, the fixing base 80 is disposed on an appropriate position of an operation bed (not shown). The sleeves 83 are used to adjust angles. The adjusting member 81 is rotated to tighten the tightwire 82, urging the sleeves 83 to abut against each other. The sleeves 83 cooperate with the tightwire 82 to define an angle and a position. The operation auxiliary tools (not shown) are mounted on the clamp 84.

However, the tightwire 82 tends to be loosened and is difficult to control when it has been loosened. When the surgeon wants to adjust the angle by the sleeves 83, it is necessary to rotate the adjusting member 81 as well as to adjust link angles of the sleeves 83. The adjusting process is cumbersome. Moreover, the sleeves 83 have to be positioned by stretching the tightwire 82 tightly. If the external force is excessively large or the tightwire 82 is employed continuously in a long term, the tightwire 82 is probably loosened and even broken. In these cases, the conventional support mechanism 8 can not meet the demand of the surgical operations.

SUMMARY OF THE INVENTION

To overcome the shortcomings, an object of the present invention is to provide a support mechanism for operation auxiliary tools which maintains predetermined angles and positions to support operation auxiliary tools, thereby ensuring operations stable.

The support mechanism for operation auxiliary tools comprises a fixing unit, a support lever movably mounted on the fixing unit, a first bar movably connecting with an end of the support lever, a limiting unit engaging with another end of the first bar, and a second bar connecting with the limiting unit. The first bar includes at least a first sleeve with an end movably connecting with the support lever, a first sheath pole on another end of the first sleeve, a first push pole in the sheath pole, and a first push portion in the first sleeve. The first push portion has two ends respectively corresponding to the support lever and the first push pole. The limiting unit includes an upper shaft base and a lower shaft base movably connecting with each other, an interferential portion in the upper shaft base and corresponding to another end of the first push pole of the first bar, an abut portion in the lower shaft base, a link pole connecting with the abut portion and extending beyond the upper shaft base, and a rotation button connecting with the link pole. The second bar includes at least a second sheath pole with an end in the lower shaft base, a second push pole being provided in the second sheath pole and having an end corresponding to the abut portion, a second sleeve on another end of the second sheath pole, a clamp movably connecting with the second sleeve, a second push portion in the second sleeve. The second push portion has two ends respectively corresponding to the second push pole and an end of the clamp.

DESCRIPTION OF THE PREFERRED EMBODIMENTS

Figure 1:
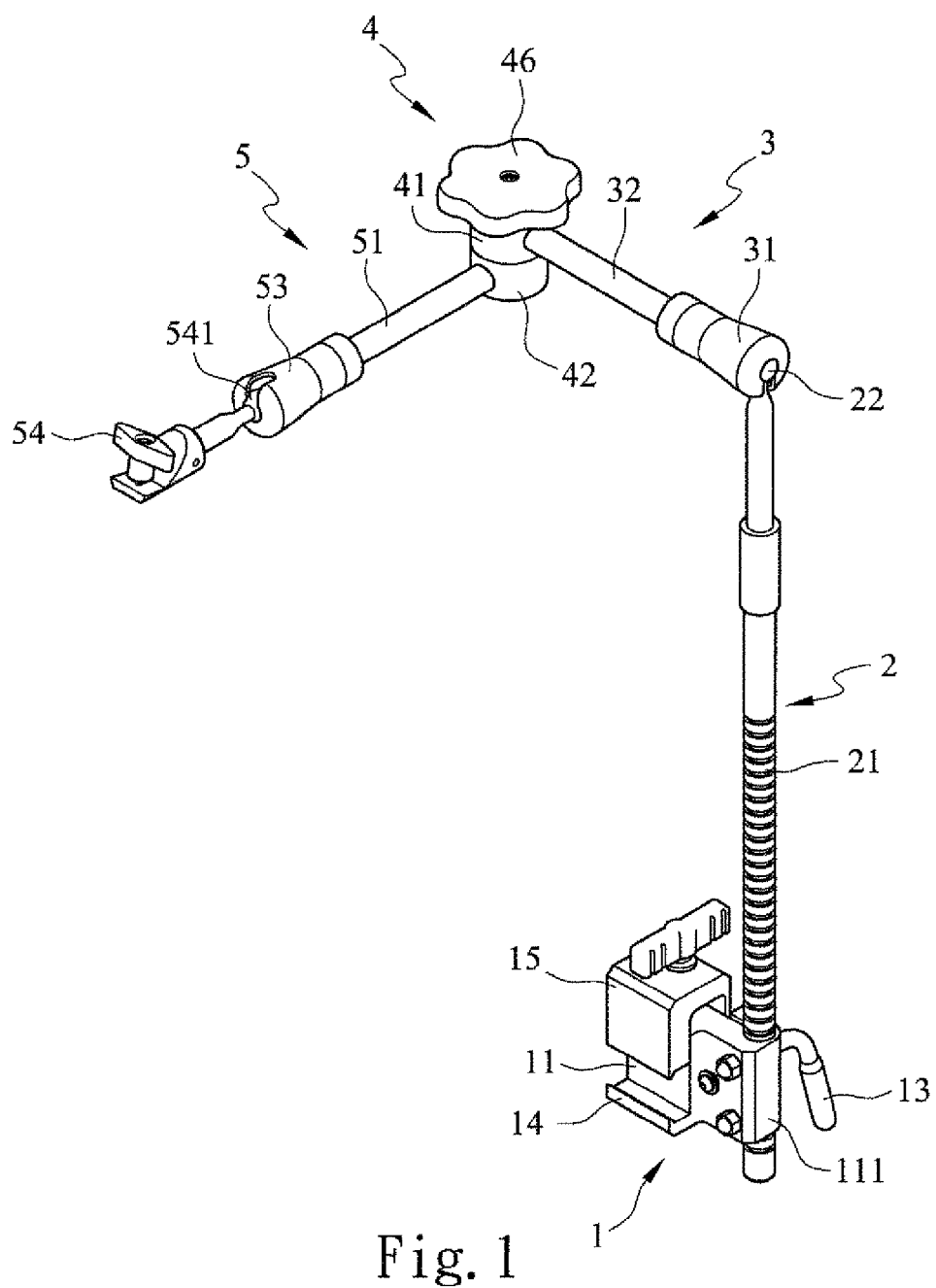
FIG. 1 is a perspective view of a support mechanism for operation auxiliary tools of the present invention.
Figure 2:
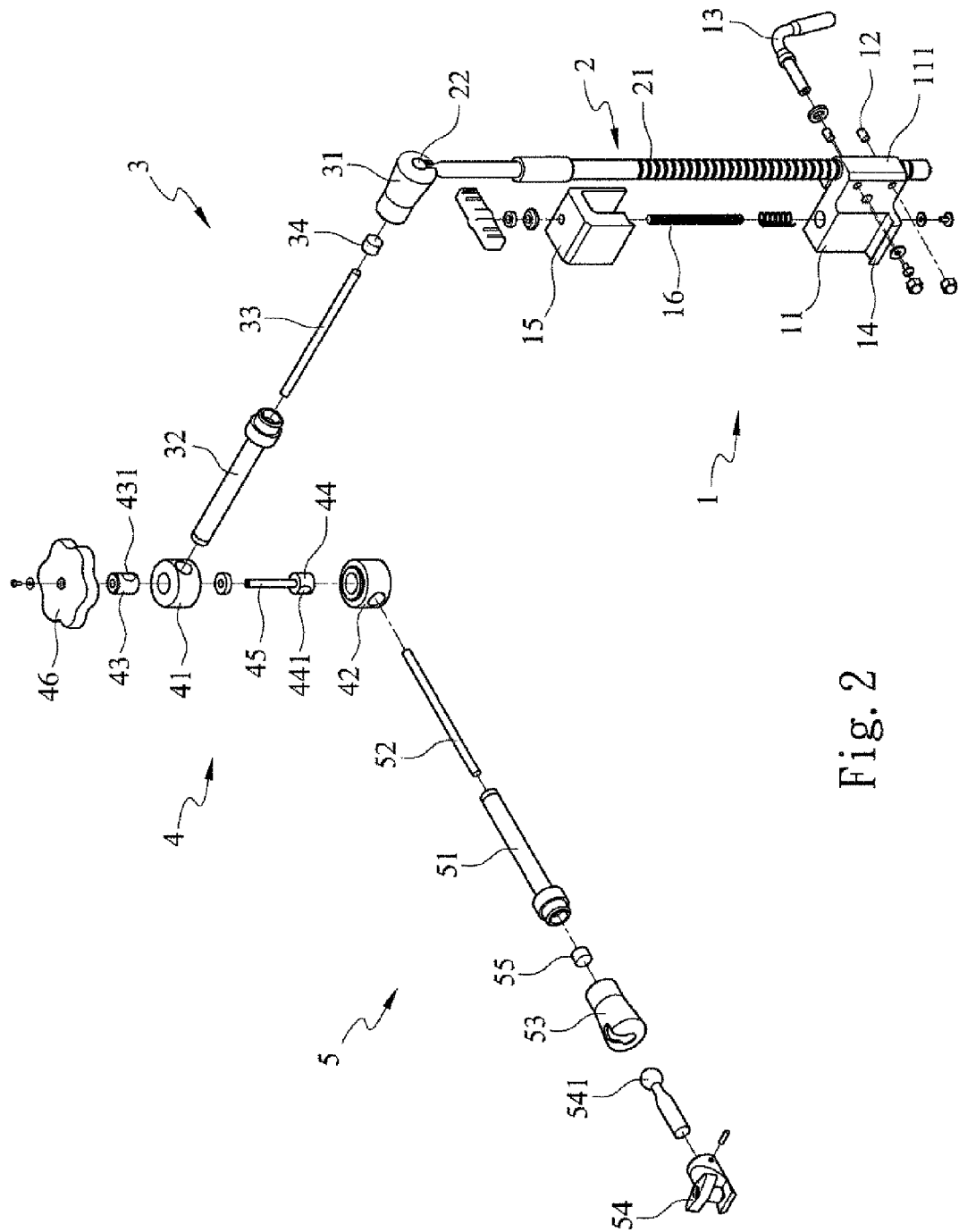
FIG. 2 is an exploded view of FIG. 1.

With reference to FIGS. 1 and 2, a support mechanism for operation auxiliary tools comprises a fixing unit 1, a support lever 2, a first bar 3, a limiting unit 4 and a second bar 5.

The fixing unit 1 comprises at least a fixing base 11, a positioning portion 12 provided on the fixing base 11, an action portion 13 mounted on the fixing base 11, an extension portion 14 extending from a bottom of the fixing base 11, and a lock portion 15 locking with the fixing base 11 for corresponding to the extension portion 14. The fixing base 11 forms a holding portion 111 on a side thereof, the positioning portion 12 communicating with the holding portion 111. The action portion 13 links with the holding portion 111 of the fixing base 11. The lock portion 15 forms an adjusting lever 16 thereon.

The support lever 2 is movably mounted through the holding portion 111 of the fixing base 11. A plurality of rib rings 21 are provided on the support lever 2 for interferentially fitting to the positioning portion 12. A first ball 22 is provided on an end of the support lever 2.

The first bar 3 movably connects with an end of the support lever 2, and includes at least a first sleeve 31 with an end movably connecting with the first ball 22 of the support lever 2, a first sheath pole 32 on another end of the first sleeve 31, a first push pole 33 in the sheath pole 32, and a first push portion 34 in the first sleeve 31. The first push portion 34 has two ends respectively corresponding to the support lever 2 and the first push pole 33.

The limiting unit 4 engages with another end of the first bar 3 and opposite to the support lever 2. The limiting unit 4 includes an upper shaft base 41 and a lower shaft base 42 movably connecting with each other, an interferential portion 43 in the upper shaft base 41, an abut portion 44 in the lower shaft base 42, a link pole 45 connecting with the abut portion 44 and extending beyond the upper shaft base 41, and a rotation button 46 connecting with the link pole 45. The interferential portion 43 corresponds to another end of the first push pole 33 of the first bar 3 and opposite to the first push portion 34. The interferential portion 43 forms a first recess 431 on an outer peripheral thereof and corresponding to an end of the first push pole 33. The abut portion 44 forms a second recess 441 on an outer peripheral thereof.

The second bar 5 connects with the limiting unit 4, and includes at least a second sheath pole 51 with an end in the lower shaft base 42, a second push pole 52 in the second sheath pole 51, a second sleeve 53 on another end of the second sheath pole 51, a clamp 54 movably connecting with the second sleeve 53, a second push portion 55 in the second sleeve 53. The second push pole 52 has an end corresponding to the second recess 441 of the abut portion 44. The second push portion 55 has two ends respectively corresponding to the second push pole 52 and an end of the clamp 54. A second ball 541 is provided on an end of the clamp 54 and movably engages with the second sleeve 53.

Figure 3:
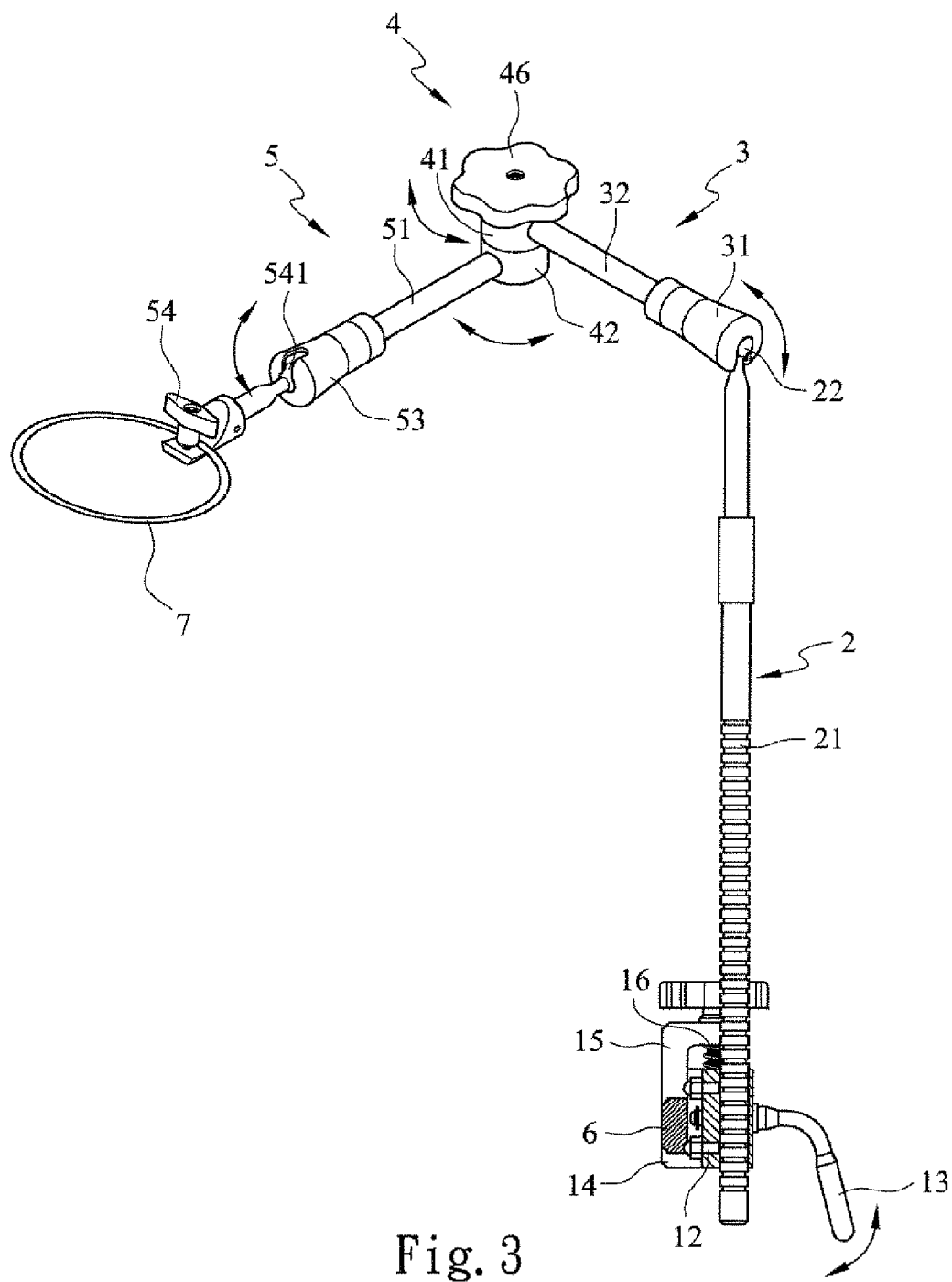
FIG. 3 shows an operation state of the support mechanism of FIG. 1.
Figure 4:
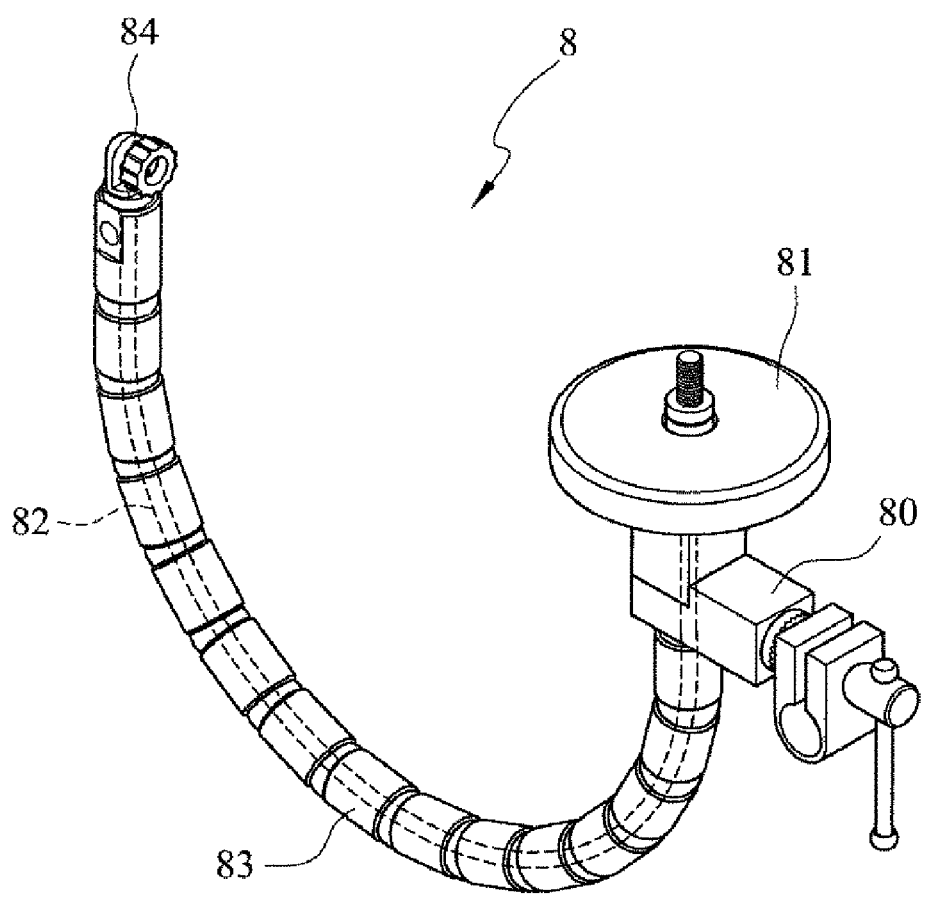
FIG. 4 is a perspective view of a conventional support mechanism for operation auxiliary tools.

Referring to FIG. 2 and FIG. 3, in use, the extension portion 14 of the fixing unit 1 cooperates with the lock portion 15 and is placed on a transverse side bar 6 of an operation bed. The lock portion 15 cooperates with the adjusting lever 16 to serve as locking and unlocking elements, whereby the fixing unit 1 is freely fixed to any appropriate position of the transverse side bar 6. The support lever 2 moves according to demand of operations, and moves up and down along the holding portion 111 of the fixing base 11. When an appropriate position is determined, the positioning portion 12 interferentially fits to the rib rings 21 of the support lever 2. The action portion 13 is rotated to drive the holding portion 111 and to retain the support lever 2. Thus, the fixing unit 1 and the support lever 2 are adjusted to a desired height.

in order to adjust the first bar 3, the second bar 5 and the clamp 54, the first sleeve 31 of the first bar 3 cooperates with the first ball 22 of the support lever 2, and with the upper shaft base 41 and the lower shaft base 42 of the limiting unit 4. The second sleeve 53 of the second bar 5 cooperates with the second ball 541 of the clamp 54. By this means, the first bar 3, the second bar 5 and the clamp 54 are adjusted based on original positions. When an appropriate position is determined, the rotation button 46 of the limiting unit 4 is rotated and brings the link pole 45 to rotate. Meanwhile the interferential portion 43 and the abut portion 44 are brought to move. The first recess 431 of the interferential portion 43 and the second recess 441 of the abut portion 44 respectively depart from the first push pole 33 of the first bar 3 and the second push pole 52 of the second bar 5. The first push pole 33 of the first bar 3 and the second push pole 52 of the second bar 5 are pushed by the interferential portion 43 and the abut portion 44. The first push pole 33 of the first bar 3 and the second push pole 52 of the second bar 5 push the first push portion 34 and the second push portion 55 simultaneously. The first push portion 34 and the second push portion 55 respectively abut against the first ball 22 of the support lever 2 and the second ball 541 of the clamp 54. The first bar 3, the second bar 5 and the clamp 54 are positioned with desired angles. Operation auxiliary tools 7 can be placed on the clamp 54. The limiting unit 4 restrains the freedom of the first bar 3 and the second bar 5 simultaneously. The support mechanism is placed firmly with a predetermined angle and position, making operations more stable.

The fixing unit 1 combines with the operation bed, and operation auxiliary tools 7 are placed on the second bar 5. The first bar 3, the second bar 5 and the clamp 54 are adjusted and then positioned by the limiting unit 4. The limiting unit 4 maintains the support lever 2, the first bar 3 and the second bar 5 at desired freedom. The support mechanism is placed firmly with a predetermined angle and position, making operations more stable.

It is understood that the invention may be embodied in other forms without departing from the spirit thereof. Thus, the present examples and embodiments are to be considered in all respects as illustrative and not restrictive, and the invention is not to be limited to the details given herein.

What is claimed is:

1. A support mechanism for operation auxiliary tools, comprising;
   a fixing unit;
   a support lever movably mounted on the fixing unit;
   a first bar movably connecting with an end of the support lever, and including at least a first sleeve with an end movably connecting with the support lever, a first sheath pole on another end of the first sleeve, a first push pole in the sheath pole, and a first push portion in the first sleeve, the first push portion having two ends respectively corresponding to the support lever and the first push pole;
   a limiting unit engaging with another end of the first bar, and including an upper shaft base and a lower shaft base movably connecting with each other, an interferential portion in the upper shaft base and corresponding to another end of the first push pole of the first bar, an abut portion in the lower shaft base, a link pole connecting with the abut portion and extending beyond the upper shaft base, and a rotation button connecting with the link pole; and
   a second bar connecting with the limiting unit, and including at least a second sheath pole with an end in the lower shaft base, a second push pole being provided in the second sheath pole and having an end corresponding to the abut portion, a second sleeve on another end of the second sheath pole, a clamp movably connecting with the second sleeve, a second push portion in the second sleeve, the second push portion having two ends respectively corresponding to the second push pole and an end of the clamp.

2. The support mechanism for operation auxiliary tools as claimed in claim 1, wherein the fixing unit comprises at least a fixing base with a holding portion on a side thereof for movably connecting with the support lever, a positioning portion being provided on the fixing base and communicating with the holding portion, an action portion linking with the holding portion of the fixing base, an extension portion on an appropriate position of a bottom of the fixing base, and a lock portion locking with the fixing base for corresponding to the extension portion.

3. The support mechanism for operation auxiliary tools as claimed in claim 2, wherein the lock portion forms an adjusting lever thereon.

4. The support mechanism for operation auxiliary tools as claimed in claim 1, wherein a plurality of rib rings are provided on the support lever, and a first ball is provided on an end of the support lever for movably connecting with the first sleeve.

5. The support mechanism for operation auxiliary tools as claimed in claim 1, wherein the interferential portion forms a first recess on an outer peripheral thereof for corresponding to an end of the first push pole of the first bar.

6. The support mechanism for operation auxiliary tools as claimed in claim 1, wherein the abut portion forms a second recess on an outer peripheral thereof for corresponding to an end of the second push pole of the second bar.

7. The support mechanism for operation auxiliary tools as claimed in claim 1, wherein a second ball is provided on an end of the clamp and movably engages with the second sleeve.

* * * * *